United States Patent
Mori et al.

(10) Patent No.: US 11,571,683 B2
(45) Date of Patent: *Feb. 7, 2023

(54) HONEYCOMB-STRUCTURED CATALYST FOR ORGANIC SUBSTANCE DECOMPOSITION AND ORGANIC SUBSTANCE DECOMPOSING APPARATUS

(71) Applicant: Murata Manufacturing Co., Ltd., Nagaokakyo (JP)

(72) Inventors: Naoya Mori, Nagaokakyo (JP); Satoshi Kuretake, Nagaokakyo (JP); Nario Sugahara, Nagaokakyo (JP); Kentaro Ishihara, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 124 days.

This patent is subject to a terminal disclaimer.

(21) Appl. No.: 17/018,869

(22) Filed: Sep. 11, 2020

(65) Prior Publication Data

US 2020/0406245 A1    Dec. 31, 2020

Related U.S. Application Data

(63) Continuation of application No. PCT/JP2019/015483, filed on Apr. 9, 2019.

(30) Foreign Application Priority Data

May 11, 2018    (JP) .............................. JP2018-092386

(51) Int. Cl.
B01J 21/04    (2006.01)
B01J 21/06    (2006.01)
(Continued)

(52) U.S. Cl.
CPC ............. *B01J 23/8892* (2013.01); *A61L 9/03* (2013.01); *B01D 53/865* (2013.01);
(Continued)

(58) Field of Classification Search
CPC .............. B01D 53/865; B01D 53/8668; B01D 53/8687; B01D 53/8696; B01J 21/04;
(Continued)

(56) References Cited

U.S. PATENT DOCUMENTS 3,644,147 A * 2/1972 Young, II ................. B01J 35/00
429/528
5,380,692 A * 1/1995 Nakatsuji ............... B01J 23/002
502/313

(Continued)

FOREIGN PATENT DOCUMENTS

JP    H0780310 A    3/1995
JP    2000140635 A    5/2000
(Continued)

OTHER PUBLICATIONS

International Search Report issued for PCT/JP2018/045261, dated Feb. 5, 2019.

(Continued)

*Primary Examiner* — Cam N. Nguyen
(74) *Attorney, Agent, or Firm* — ArentFox Schiff LLP

(57) ABSTRACT

A honeycomb-structured catalyst for decomposing an organic substance, which includes a catalyst particle. The catalyst particle contains a perovskite-type composite oxide represented by $A_xB_yM_zO_w$, where the A contains at least of Ba and Sr, the B contains Zr, the M is at least one of Mn, Co, Ni, and Fe, $y+z=1$, $1.001 \leq x \leq 1.05$, $0.05 \leq z \leq 0.2$, and w is a positive value that satisfies electrical neutrality. The toluene decomposition rate is greater than 90% when toluene is decomposed using the honeycomb-structured catalyst sub- (Continued)

jected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C.

12 Claims, 4 Drawing Sheets

(51) Int. Cl.
| | |
|---|---|
| B01J 23/00 | (2006.01) |
| B01J 23/34 | (2006.01) |
| B01J 23/68 | (2006.01) |
| B01J 23/78 | (2006.01) |
| B01J 23/88 | (2006.01) |
| B01J 35/02 | (2006.01) |
| B01J 35/04 | (2006.01) |
| B01J 35/10 | (2006.01) |
| B01D 53/86 | (2006.01) |
| B01D 53/94 | (2006.01) |
| A61L 9/03 | (2006.01) |
| B01J 23/889 | (2006.01) |
| C01G 45/12 | (2006.01) |
| C01G 51/00 | (2006.01) |
| C01G 53/00 | (2006.01) |
| B01J 37/00 | (2006.01) |
| B01J 21/16 | (2006.01) |

(52) U.S. Cl.
CPC ..... *B01D 53/8668* (2013.01); *B01D 53/8687* (2013.01); *B01D 53/8696* (2013.01); *B01D 53/94* (2013.01); *B01J 21/04* (2013.01); *B01J 21/066* (2013.01); *B01J 23/002* (2013.01); *B01J 23/34* (2013.01); *B01J 23/688* (2013.01); *B01J 23/78* (2013.01); *B01J 35/026* (2013.01); *B01J 35/04* (2013.01); *B01J 35/1009* (2013.01); *B01J 35/1038* (2013.01); *B01J 35/1061* (2013.01); *B01J 35/1066* (2013.01); *B01J 35/1071* (2013.01); *B01J 35/1076* (2013.01); *C01G 45/125* (2013.01); *C01G 45/1207* (2013.01); *C01G 51/66* (2013.01); *C01G 53/66* (2013.01); *B01D 2255/104* (2013.01); *B01D 2255/2042* (2013.01); *B01D 2255/2047* (2013.01); *B01D 2255/2061* (2013.01); *B01D 2255/2063* (2013.01); *B01D 2255/2073* (2013.01); *B01D 2255/2092* (2013.01); *B01D 2255/2094* (2013.01); *B01D 2255/20707* (2013.01); *B01D 2255/20715* (2013.01); *B01D 2255/20738* (2013.01); *B01D 2255/20746* (2013.01); *B01D 2255/20753* (2013.01); *B01D 2255/20792* (2013.01); *B01D 2255/402* (2013.01); *B01D 2255/9202* (2013.01); *B01D 2255/9207* (2013.01); *B01D 2257/7027* (2013.01); *B01D 2258/01* (2013.01); *B01D 2258/02* (2013.01); *B01J 21/16* (2013.01); *B01J 37/009* (2013.01); *C01P 2002/34* (2013.01); *C01P 2002/50* (2013.01); *C01P 2002/72* (2013.01); *C01P 2002/77* (2013.01); *C01P 2006/12* (2013.01); *C01P 2006/14* (2013.01); *C01P 2006/16* (2013.01)

(58) Field of Classification Search
CPC ........ B01J 21/066; B01J 23/002; B01J 23/34; B01J 23/688; B01J 23/78; B01J 23/8892; B01J 35/026; B01J 35/04; B01J 35/1009; B01J 35/1038; B01J 35/1061; B01J 35/1066; B01J 35/1071; B01J 35/1076; A61L 9/03; C01G 51/66; C01G 53/66; C01G 45/125; C01G 45/1207
See application file for complete search history.

(56) References Cited

U.S. PATENT DOCUMENTS

| | | | | |
|---|---|---|---|---|
| 6,060,420 | A * | 5/2000 | Munakata | ............... B01J 23/002 502/328 |
| 8,123,931 | B2 * | 2/2012 | Kang | ..................... C10G 11/20 585/653 |
| 8,329,612 | B2 | 12/2012 | Sato et al. | |
| 8,569,200 | B2 * | 10/2013 | Kang | ..................... B01J 37/031 585/653 |
| 2002/0035035 | A1 | 3/2002 | Kirchnerova et al. | |
| 2007/0027031 | A1 | 2/2007 | Ikeda et al. | |
| 2007/0249497 | A1 | 10/2007 | Tanaka et al. | |
| 2009/0108239 | A1 | 4/2009 | Caro et al. | |
| 2009/0131252 | A1 | 5/2009 | Tanaka et al. | |
| 2009/0286677 | A1 | 11/2009 | Takeshima et al. | |
| 2009/0286680 | A1 * | 11/2009 | Hirano | ................. B01J 37/0221 502/326 |
| 2010/0139152 | A1 * | 6/2010 | Hucul | ..................... C11C 3/10 44/388 |
| 2012/0074357 | A1 | 3/2012 | Sato et al. | |
| 2016/0115835 | A1 | 4/2016 | Daido et al. | |

FOREIGN PATENT DOCUMENTS

| | | |
|---|---|---|
| JP | 3406001 B2 | 5/2003 |
| JP | 2006231280 A | 9/2006 |
| JP | 2006346603 A | 12/2006 |
| JP | 2006347825 A | 12/2006 |
| JP | 5076377 B2 | 11/2012 |
| JP | 2013244479 A | 12/2013 |
| JP | 2015229137 A | 12/2015 |
| JP | 6036276 B2 | 11/2016 |
| WO | 0016900 A1 | 3/2000 |
| WO | 2004096436 A1 | 11/2004 |
| WO | 2005058490 A1 | 6/2005 |
| WO | 2010143676 A1 | 12/2010 |
| WO | 2014189115 A1 | 11/2014 |
| WO | 2015194451 A1 | 12/2015 |

OTHER PUBLICATIONS

Kirchenerova, J. et al.; "Design criteria for high-temperature combustion catalysts"; Catalysis Letters, Jul. 2000, vol. 67, No. 2-4, pp. 175-181.
International Search Report issued for PCT/JP2019/017674, dated Jul. 16, 2019.
International Search Report issued for PCT/JP2019/015483, dated Jul. 16, 2019.
International Search Report issued for PCT/JP2019/008692, dated May 21, 2019.
International Search Report issued for PCT/JP2019/008593, dated May 21, 2019.
Written Opinion of the International Searching Authority issued for PCT/JP2019/008593, dated May 21, 2019.
Written Opinion of the International Searching Authority issued for PCT/JP2019/008592, dated May 21, 2019.
Written Opinion of the International Searching Authority issued for PCT/JP2019/015483, dated Jul. 16, 2019.
Written Opinion of the International Searching Authority issued for PCT/JP2019/017674, dated Jul. 16, 2019.
Written Opinion of the International Searching Authority issued for PCT/JP2018/045261, dated Feb. 5, 2019.
Gallucci, Katia et al.; "Catalytic combustion of methane on $BaZr_{(1-x)}Me_xO_3$ perovskites synthesized by a modified citrate method"; Catalysis Today, 2012, vol. 197, No. 1, pp. 236-242.
Tuyen, Nguyen Van et al.; "Interaction of Hydrogen with Perovskite-supported Metal Catalysts: I. $M/Sr_{1-x}Zr_{1-y}O_{3-\alpha}$ (M = Cu, Pd)"; Kinetics and Catalysis, 1996, vol. 37, No. 4, pp. 575-578.

(56) References Cited

OTHER PUBLICATIONS

Japanese Office Action issued for Japanese Application No. 2020-518162, dated Jun. 29, 2021.
Yuxi Liu et al.; "Controlled preparation and high catalytic performance of three-dimensionally ordered macroporous LaMnO3 with nanovoid skeletons for the combustion of toluene"; Journal of Catalysis 287, 2012, pp. 149-160.

* cited by examiner

HONEYCOMB-STRUCTURED CATALYST FOR ORGANIC SUBSTANCE DECOMPOSITION AND ORGANIC SUBSTANCE DECOMPOSING APPARATUS

CROSS REFERENCE TO RELATED APPLICATIONS

The present application is a continuation of International application No. PCT/JP2019/015483, filed Apr. 9, 2019, which claims priority to Japanese Patent Application No. 2018-092386, filed May 11, 2018, the entire contents of each of which are incorporated herein by reference.

FIELD OF THE INVENTION

The present invention relates to a catalyst for decomposing an organic substance having a honeycomb structure and an organic substance decomposing apparatus including a honeycomb-structured catalyst for decomposing an organic substance.

BACKGROUND OF THE INVENTION

Conventionally, catalysts for decomposing organic substances have been known. It is preferable that such catalysts for decomposing organic substances have not only a high organic substance decomposition rate but also are less deteriorated after a heat treatment at a high temperature.

Patent Document 1 describes a catalyst in which an active component containing one or more elements and/or compounds selected from Group VIII metal elements or Group VIII metal oxides or an active component containing a rare earth oxide and one or more elements and/or compounds selected from Group VIII metal elements or Group VIII metal oxides is supported on a honeycomb-structured carrier obtained by extrusion molding.

However, when a noble metal is used as a highly active component as in the catalyst described in Patent Document 1, deterioration often occurs during the use of catalyst at high temperatures.

In contrast, Patent Document 2 describes a catalyst for decomposing an organic substance which does not contain a noble metal and is less deteriorated even when being subjected to a heat treatment at 800° C. for 100 hours.

Patent Document 3 describes a catalyst for exhaust gas purification in which a three-way catalyst for exhaust gas purification is supported on a heat resistant carrier.

Patent Document 1: Japanese Patent Application Laid-Open No. 2006-231280
Patent Document 2: Japanese Patent No. 6303834
Patent Document 3: Japanese Patent No. 3406001

SUMMARY OF THE INVENTION

It has been found that the heat resistance of the catalyst decreases when the catalyst for decomposing an organic substance described in Patent Document 2 is supported on a carrier by being mixed with inorganic sol and fired at a low temperature of about 600° C. as in the method described in Patent Document 3. It is considered that this is because the inorganic sol chemically reacts with the catalyst so that the original catalytically active points do not function and the specific surface area of the catalyst decreases by the sintering promoting action of the inorganic sol.

The present invention is intended to solve the above problems, and an object thereof is to provide a honeycomb-structured catalyst for decomposing an organic substance which has a high organic substance decomposition rate and can suppress its deterioration due to a heat treatment at a high temperature, and an organic substance decomposing apparatus including such a honeycomb-structured catalyst for decomposing an organic substance.

The honeycomb-structured catalyst for decomposing an organic substance of the present invention includes a catalyst particle, in which the catalyst particle contains a perovskite-type composite oxide represented by $A_xB_yM_zO_w$, where the A contains at least one selected from Ba and Sr, the B contains Zr, the M is at least one selected from Mn, Co, Ni, and Fe, $y+z=1$, $1.001 \le x \le 1.05$, $0.05 \le z \le 0.2$, w is a positive value that satisfies electrical neutrality, and a toluene decomposition rate is greater than 90% when toluene is decomposed using the honeycomb-structured catalyst subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C.

The honeycomb-structured catalyst for decomposing an organic substance according to another aspect of the present invention includes a catalyst particle, in which the catalyst particle contains a perovskite-type composite oxide represented by $A_xB_yM_zO_w$, where the A contains at least one selected from Ba and Sr, the B contains Zr, the M is at least one selected from Mn, Co, Ni, and Fe, $y+z=1$, $1.001 \le x \le 1.05$, $0.05 \le z \le 0.2$, w is a positive value that satisfies electrical neutrality, and when a toluene decomposition rate is regarded as 1 when toluene is decomposed using the honeycomb-structured catalyst before being subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C., the toluene decomposition rate when using the honeycomb-structured catalyst after being subjected to the heat treatment is greater than 0.935 and smaller than 1.

The x may satisfy $x \ge 1.005$.

The honeycomb-structured catalyst may have a structure obtained by subjecting the catalyst particle to extrusion molding.

The organic substance decomposing apparatus of the present invention includes the honeycomb-structured catalyst for decomposing an organic substance described above.

The honeycomb-structured catalyst for decomposing an organic substance of the present invention has a high organic substance decomposition rate and can suppress its deterioration due to a heat treatment at a high temperature.

The organic substance decomposing apparatus of the present invention can decompose an organic substance at a high decomposition rate even after the catalyst is subjected to a heat treatment at a high temperature since the apparatus includes a honeycomb-structured catalyst for decomposing an organic substance which has a high organic substance decomposition rate and can suppress its deterioration due to a heat treatment at a high temperature.

DETAILED DESCRIPTION OF THE INVENTION

Figure 1:
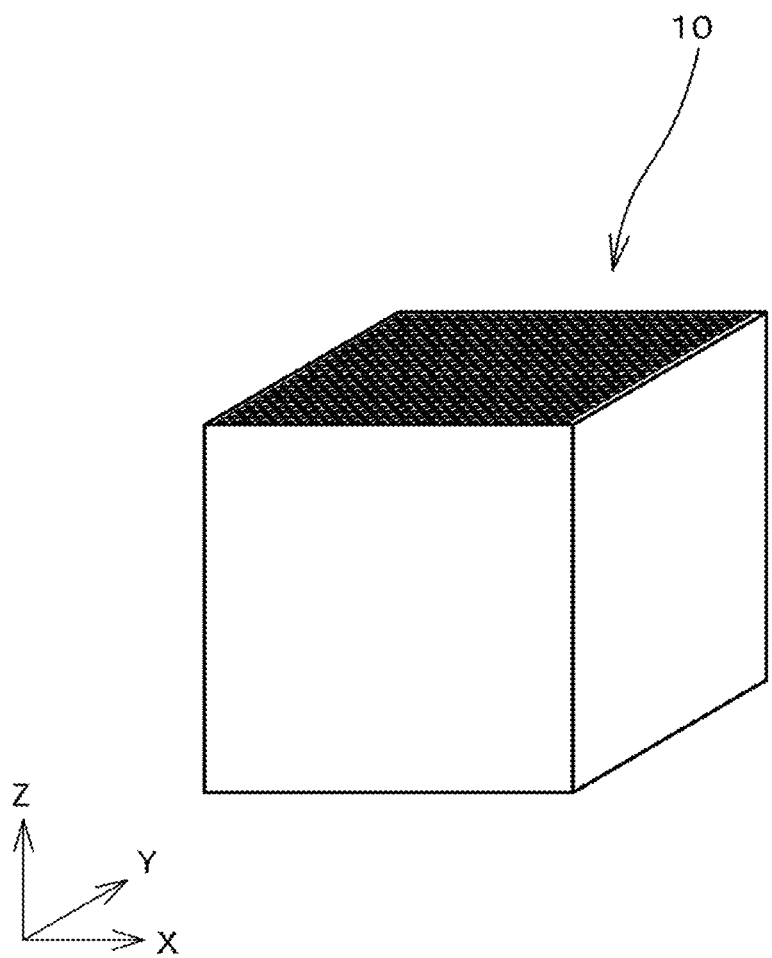
FIG. 1 is a perspective view illustrating an external shape of a honeycomb-structured catalyst for decomposing an organic substance of the present invention.

Hereinafter, the features of the present invention will be specifically described with reference to the embodiments of the present invention.

The supported catalyst for decomposing an organic substance according to the present invention satisfies at least either of the following first requirement (hereinafter, referred to as the first requirement of the present invention) or second requirement (hereinafter, referred to as the second requirement of the present invention).

A honeycomb-structured catalyst for decomposing an organic substance which satisfies the first requirement of the present invention is a honeycomb-structured catalyst which includes a catalyst particle and in which the catalyst particle contains a perovskite-type composite oxide represented by $A_xB_yM_zO_w$, where the A contains at least one selected from Ba and Sr, the B contains Zr, the M is at least one selected from Mn, Co, Ni, and Fe, $y+z=1$, $1.001 \leq x \leq 1.05$, $0.05 \leq z \leq 0.2$, w is a positive value that satisfies electrical neutrality, and a toluene decomposition rate is greater than 90% when toluene is decomposed using the honeycomb-structured catalyst subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C.

A honeycomb-structured catalyst for decomposing an organic substance which satisfies the second requirement of the present invention is a honeycomb-structured catalyst which includes a catalyst particle and in which the catalyst particle contains a perovskite-type composite oxide represented by $A_xB_yM_zO_w$, where the A contains at least one selected from Ba and Sr, the B contains Zr, the M is at least one selected from Mn, Co, Ni, and Fe, $y+z=1$, $1.001 \leq x \leq 1.05$, $0.05 \leq z \leq 0.2$, w is a positive value that satisfies electrical neutrality, and when a toluene decomposition rate is regarded as 1 when toluene is decomposed using the honeycomb-structured catalyst before being subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C., the toluene decomposition rate when using the honeycomb-structured catalyst after being subjected to the heat treatment is greater than 0.935 and smaller than 1.

A honeycomb-structured catalyst for decomposing an organic substance which satisfies at least either of the first requirement or second requirement of the present invention has a high organic substance decomposition rate and can suppress its deterioration after being subjected to a heat treatment at a high temperature such as 1200° C. as will be described later. This honeycomb-structured catalyst for decomposing an organic substance can be used in various applications to decompose organic substances such as purification of exhaust gas from factories and motor vehicles. In that case, it is possible to configure an organic substance decomposing apparatus including a honeycomb-structured catalyst for decomposing an organic substance which satisfies at least either of the first requirement or the second requirement of the present invention.

Example

Powders of high-purity $BaCO_3$, $ZrO_2$, and $MnCO_3$ were weighed so as to have the composition presented in Table 1, pure water was added thereto, and the mixture was wet-mixed together with $ZrO_2$ cobble stones to obtain a slurry. This slurry was dried at 120° C. in a dryer, and the obtained powder was then subjected to a heat treatment at 1100° C. for 2 hours to obtain the intended perovskite-type composite oxide.

Subsequently, water, a dispersant, and a lubricant were added to the perovskite-type composite oxide and the mixture was kneaded to obtain a kneaded product for extrusion molding. This kneaded product was subjected to extrusion molding to be extruded by an extrusion molding machine, and the molded product was dried and then fired in the air at a temperature of 1050° C. or more and 1700° C. or less in an electric furnace to obtain a honeycomb-structured catalyst for decomposing an organic substance. In order to attain initial activity and heat resistance, it is preferable to set the firing temperature to 1200° C. or more and 1650° C. or less. When the firing temperature is higher than 1650° C., there is a possibility that sintering proceeds too much, structural defects such as cracks are generated, and the catalytic activity decreases.

FIG. 1 is a perspective view illustrating the external shape of a honeycomb-structured catalyst for decomposing an organic substance 10 fabricated. The honeycomb-structured catalyst for decomposing an organic substance 10 is provided with a plurality of cells. As the size of the honeycomb-structured catalyst for decomposing an organic substance 10, the dimension in the X-axis direction in FIG. 1 is about 50 mm, the dimension in the Y-axis direction is about 50 mm, and the dimension in the Z-axis direction is about 50 mm. The size of the cell in the Z-axis direction in plan view is about 1.5 mm×about 1.5 mm, and the number of cells per 1 inch$^2$ is about 200.

The honeycomb-structured catalyst for decomposing an organic substance 10 has a structure obtained by subjecting the catalyst particle to extrusion molding as described above. In other words, the honeycomb-structured catalyst for decomposing an organic substance 10 does not have a structure in which the catalyst particles are supported on a carrier having a honeycomb structure.

Figure 2:
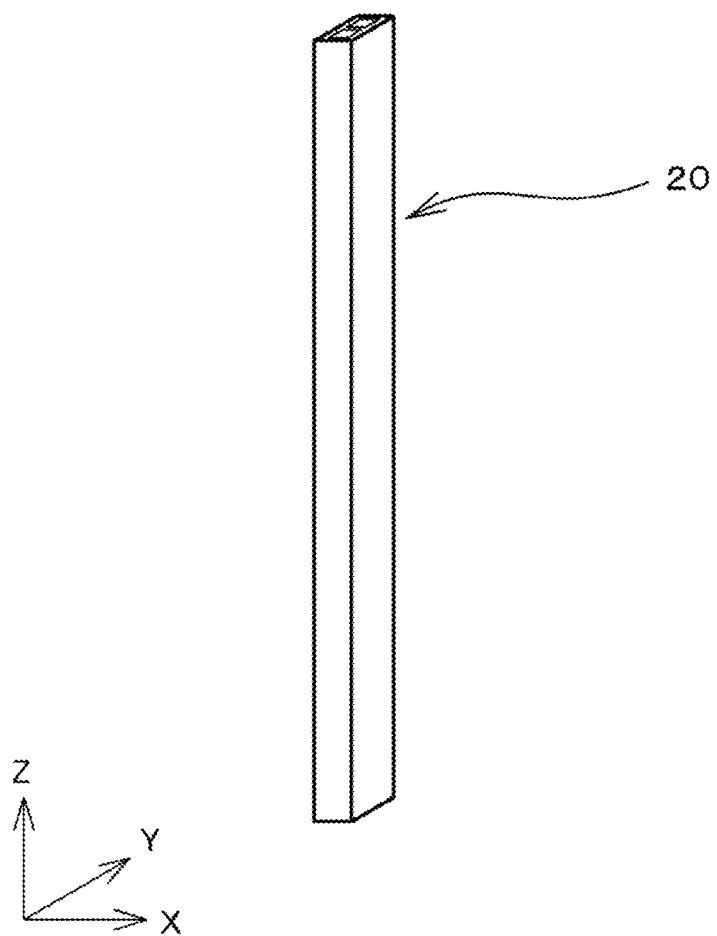
FIG. 2 is a perspective view illustrating an external shape of a catalyst sample for test.

Subsequently, a stick-like structure for two cells was cut out from the honeycomb-structured catalyst for decomposing an organic substance 10 to obtain a catalyst sample for test. FIG. 2 is a perspective view illustrating the external shape of a catalyst sample for test 20. The dimension of the catalyst sample for test 20 in the X-axis direction is about 2 mm, the dimension thereof in the Y-axis direction is about 4 mm, and the dimension thereof in the Z-axis direction is about 50 mm.

In order to examine the properties of the catalyst sample for test 20 after being subjected to a heat treatment at a high temperature, some of the catalyst samples for test 20 were further subjected to a heat treatment at 1200° C. for 48 hours in an electric furnace. In the following description, the heat treatment at 1200° C. for 48 hours is also referred to as the additional heat treatment.

By the method described above, catalyst samples for test before and after being subjected to the additional heat treatment were obtained.

<Activity Evaluating Method>

A method for evaluating the activity of the catalyst samples for test will be described.

(1) Testing Apparatus

Figure 3:
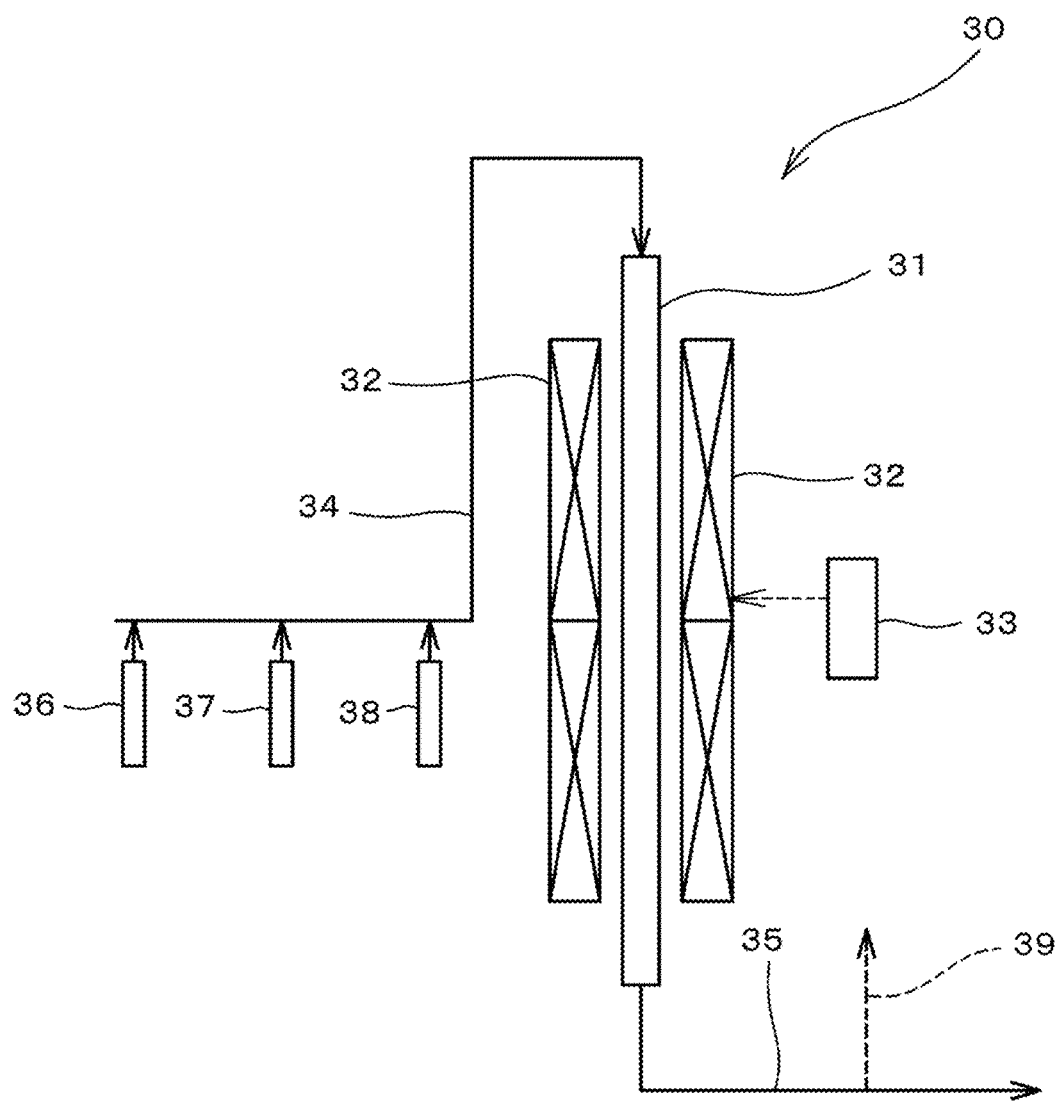
FIG. 3 is a diagram illustrating a schematic configuration of a testing apparatus used for a test to evaluate the organic substance decomposing performance of a honeycomb-structured catalyst.

FIG. 3 is a diagram illustrating a schematic configuration of a testing apparatus 30 used for a test to evaluate the organic substance decomposing performance of a honeycomb-structured catalyst for decomposing an organic substance. This testing apparatus 30 includes a pipe 31 through which an organic substance flows, a heating unit 32 for heating the organic substance flowing through the pipe 31, and a control unit 33 which controls the heating unit 32.

The catalyst sample for test 20 fabricated by the above-described method is disposed in a region to be heated by the heating unit 32 inside the pipe 31.

Figure 4:
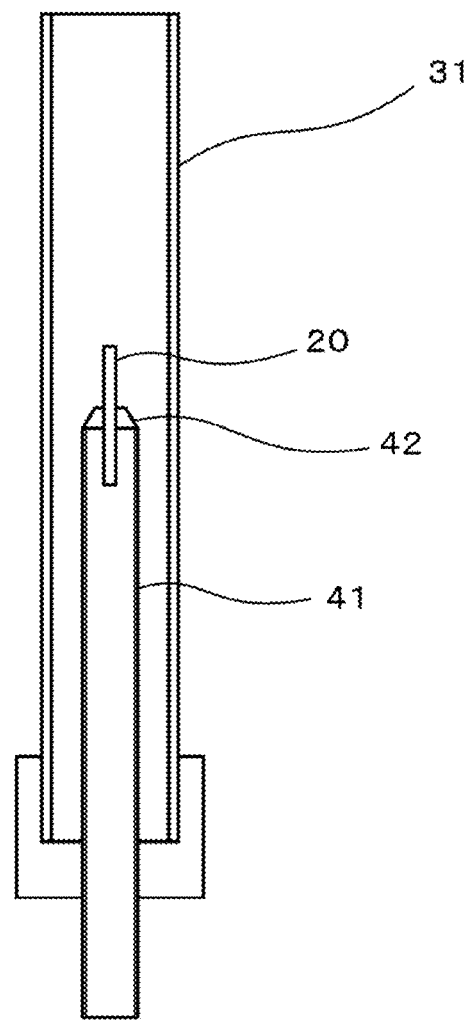
FIG. 4 is a sectional view for explaining a method for disposing a catalyst sample for test inside a pipe.

FIG. 4 is a sectional view for explaining a method for disposing the catalyst sample for test 20 inside the pipe 31. The catalyst sample for test 20 was inserted into a ¼-inch sized reaction pipe 41 up to about half the entire length and fixed and sealed using a heat-resistant inorganic adhesive 42 in that state. Thereafter, the whole reaction pipe 41 in which the catalyst sample for test 20 was inserted was inserted into the ½-inch sized pipe 31.

The pipe 31 and the reaction pipe 41 have a double pipe structure, and the gas to be treated which is supplied to the pipe 31 passes through only the interior of the catalyst sample for test 20 and is discharged to a gas discharge pipe 35 to be described later.

A gas supply pipe 34 is connected on the upstream side of the pipe 31. A toluene supply line 36 for supplying toluene (organic substance), a nitrogen supply line 37 for supplying nitrogen ($N_2$), and an oxygen supply line 38 for supplying oxygen ($O_2$) are connected to the gas supply pipe 34. In other words, the gas to be treated which contains toluene, nitrogen, and oxygen is supplied to the pipe 31 via the gas supply pipe 34.

The gas discharge pipe 35 for discharging the treated gas after passed through the interior of the catalyst sample for test 20 and being subjected to the decomposition of organic substance to the outside of the system is connected on the downstream side of the pipe 31. A sampling line 39 for sampling the treated gas is connected to the gas discharge pipe 35, and the testing apparatus is configured so that the concentration of toluene in the treated gas can be analyzed by gas chromatography.

The control unit 33 is configured so that the temperature of the region heated by the heating unit 32 can be controlled.

(2) Testing Method

Using the testing apparatus 30 described above, a test was conducted in which a gas to be treated which contained toluene, nitrogen, and oxygen was continuously supplied to the pipe 31 and toluene was decomposed. The composition of the gas to be treated was set to toluene ($CH_7H_8$): 50 ppm, nitrogen ($N_2$): 80%, and oxygen ($O_2$): 20% as a volume concentration, the space velocity SV at the time of measurement was set to 30000/h, and the catalyst temperature was set to 400° C.

The treated gas was sampled at the outlet of the sampling line 39, and the toluene concentration was quantified through analysis by gas chromatography. The toluene decomposition rate was determined based on the following Equation (1). In Equation (1), "50" is the concentration of toluene contained in the gas to be treated before being subjected to the treatment.

$$\text{Toluene decomposition rate (\%)} = 100 - 100 \times (\text{toluene concentration}/50) \quad (1)$$

The deterioration rate of the toluene decomposition rate by an additional heat treatment was calculated according to the following Equation (2), where C1 denoted the toluene decomposition rate in the case of using the catalyst sample for test 20 before being subjected to the additional heat treatment and C2 denoted the toluene decomposition rate in the case of using the catalyst sample for test 20 after being subjected to the additional heat treatment.

$$\text{Deterioration rate (\%)} = 100 - 100 \times (C2/C1) \quad (2)$$

The condition that "when a toluene decomposition rate is regarded as 1 when toluene is decomposed using the honeycomb-structured catalyst before being subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C., the toluene decomposition rate when using the honeycomb-structured catalyst after being subjected to the heat treatment is greater than 0.935 and smaller than 1" in the second requirement of the present invention is equivalent to that the deterioration rate is greater than 0% and smaller than 6.5%.

The properties of the honeycomb-structured catalysts of Sample Nos. 1 to 22 fabricated are presented in Table 1.

TABLE 1

| Sample No. | Charged composition ratio | | | | A (x) | B (y) | M (z) | |
|---|---|---|---|---|---|---|---|---|
| | x | y | z | y + z | Ba | Sr | Zr | Mn | Co |
| 1* | 0.995 | 0.900 | 0.100 | 1.000 | 1.000 | | 1.000 | 1.000 |
| 2* | 1.000 | 0.900 | 0.100 | 1.000 | 1.000 | | 1.000 | 1.000 |
| 3 | 1.001 | 0.900 | 0.100 | 1.000 | 1.000 | | 1.000 | 1.000 |
| 4 | 1.005 | 0.900 | 0.100 | 1.000 | 1.000 | | 1.000 | 1.000 |
| 5 | 1.010 | 0.900 | 0.100 | 1.000 | 1.000 | | 1.000 | 1.000 |
| 6 | 1.050 | 0.900 | 0.100 | 1.000 | 1.000 | | 1.000 | 1.000 |
| 7* | 1.100 | 0.900 | 0.100 | 1.000 | 1.000 | | 1.000 | 1.000 |
| 8* | 1.001 | 0.980 | 0.020 | 1.000 | 1.000 | | 1.000 | 1.000 |
| 9 | 1.001 | 0.950 | 0.050 | 1.000 | 1.000 | | 1.000 | 1.000 |
| 10 | 1.001 | 0.800 | 0.200 | 1.000 | 1.000 | | 1.000 | 1.000 |
| 11* | 1.001 | 0.600 | 0.400 | 1.000 | 1.000 | | 1.000 | 1.000 |
| 12* | 1.050 | 0.980 | 0.020 | 1.000 | 1.000 | | 1.000 | 1.000 |
| 13 | 1.050 | 0.950 | 0.050 | 1.000 | 1.000 | | 1.000 | 1.000 |
| 14 | 1.050 | 0.800 | 0.200 | 1.000 | 1.000 | | 1.000 | 1.000 |
| 15* | 1.050 | 0.600 | 0.400 | 1.000 | 1.000 | | 1.000 | 1.000 |
| 16* | 1.010 | 0.900 | 0.100 | 1.000 | 1.000 | | 1.000 | 1.000 |
| 17 | 1.010 | 0.900 | 0.100 | 1.000 | 1.000 | | 1.000 | 1.000 |
| 18 | 1.010 | 0.900 | 0.100 | 1.000 | 1.000 | | 1.000 | 1.000 |
| 19 | 1.010 | 0.900 | 0.100 | 1.000 | 1.000 | | 1.000 | 1.000 |
| 5 | 1.010 | 0.900 | 0.100 | 1.000 | 1.000 | | 1.000 | 1.000 |
| 20 | 1.010 | 0.900 | 0.100 | 1.000 | 1.000 | | 1.000 | 1.000 |
| 21 | 1.010 | 0.900 | 0.100 | 1.000 | 1.000 | | 1.000 | 1.000 |
| 22* | 1.010 | 0.900 | 0.100 | 1.000 | 1.000 | | 1.000 | 1.000 |

| Sample No. | M (z) | | Firing temperature (° C.) | Toluene decomposition rate (%) | | Deterioration rate % |
|---|---|---|---|---|---|---|
| | Ni | Fe | | Before additional heat treatment | After additional heat treatment | |
| 1* | | | 1500 | 96.1 | 88.0 | 8.4 |
| 2* | | | 1500 | 97.2 | 89.9 | 7.5 |
| 3 | | | 1500 | 97.8 | 94.3 | 3.6 |
| 4 | | | 1500 | 99.0 | 97.5 | 1.5 |
| 5 | | | 1500 | 99.4 | 97.9 | 1.5 |
| 6 | | | 1500 | 98.5 | 97.5 | 1.0 |
| 7* | | | 1500 | 87.1 | 85.4 | 2.0 |
| 8* | | | 1500 | 85.9 | 84.3 | 1.8 |
| 9 | | | 1500 | 97.1 | 95.3 | 1.8 |
| 10 | | | 1500 | 99.2 | 96.0 | 3.2 |
| 11* | | | 1500 | 97.9 | 86.7 | 11.4 |

TABLE 1-continued

| | | | | |
|---|---|---|---|---|
| 12* | 1500 | 87.8 | 86.9 | 1.0 |
| 13 | 1500 | 98.2 | 97.1 | 1.1 |
| 14 | 1500 | 99.7 | 98.1 | 1.6 |
| 15* | 1500 | 98.9 | 89.1 | 9.9 |
| 16* | 1000 | — | — | — |
| 17 | 1050 | 99.8 | 97.8 | 2.0 |
| 18 | 1200 | 99.6 | 98.6 | 1.0 |
| 19 | 1400 | 99.3 | 98.3 | 1.0 |
| 5 | 1500 | 99.4 | 97.9 | 1.5 |
| 20 | 1600 | 97.2 | 96.7 | 0.5 |
| 21 | 1650 | 92.0 | 91.3 | 0.8 |
| 22* | 1700 | — | — | — |

In Table 1, the composition of catalyst, firing temperature, toluene decomposition rate before and after additional heat treatment, and deterioration rate are presented respectively. In Table 1, samples in which * is attached to Sample No. are samples which do not satisfy both of the first requirement and second requirement of the present invention described above and samples in which * is not attached to Sample No. are samples which satisfy both of the first requirement and the second requirement of the present invention described above.

In the honeycomb-structured catalysts of Sample Nos. 1 to 22 in Table 1, A of the perovskite-type composite oxide represented by a general formula $A_xB_yM_zO_w$ is Ba, B is Zr, and M is Mn.

The honeycomb-structured catalysts of Sample Nos. 1 to 7 are samples in which the compositions y and z are the same as one another but the composition x is different from one another. In the honeycomb-structured catalysts Sample Nos. 3 to 6 which satisfied the first requirement and second requirement of the present invention, the toluene decomposition rates before and after the additional heat treatment were greater than 90% and the deterioration rate after the additional heat treatment was a value lower than 6.5%, more specifically 3.6% or less.

In contrast, in the honeycomb-structured catalysts of Sample Nos. 1, 2, and 7 in which the composition x was out of the range of $1.001 \leq x \leq 1.05$ and the first requirement and second requirement of the present invention were not satisfied, the toluene decomposition rate after the additional heat treatment was 90% or less. The deterioration rate after the additional heat treatment was greater than 6.5% in the honeycomb-structured catalysts of Sample Nos. 1 and 2. In the honeycomb-structured catalyst of Sample No. 7, the deterioration rate after the additional heat treatment was 2.0% to be low but the toluene decomposition rates before and after the additional heat treatment were 90% or less, more specifically 87.1% or less to be a low value.

Among the honeycomb-structured catalysts of Sample Nos. 3 to 6 which satisfied the first requirement and second requirement of the present invention, in the honeycomb-structured catalysts of Sample Nos. 4 to 6 in which the composition x satisfied the relation of $x \geq 1.005$, the deterioration rate after the additional heat treatment was 1.5% or less to be still lower.

Hence, in the honeycomb-structured catalyst which satisfies at least either of the first requirement or second requirement of the present invention, it is preferable that the composition x further satisfies the relation of $x \geq 1.005$.

The honeycomb-structured catalysts of Sample Nos. 8 to 11 are samples in which the composition x is 1.001 and the compositions y and z are different from one another. In the honeycomb-structured catalysts of Sample Nos. 9 and 10 which satisfied the first requirement and second requirement of the present invention, the toluene decomposition rates before and after the additional heat treatment were greater than 90% and the deterioration rate after the additional heat treatment was a value lower than 6.5%, specifically 3.2% or less.

In contrast, in the honeycomb-structured catalysts of Sample Nos. 8 and 11 in which the composition z was out of the range of $0.05 \leq z \leq 0.2$ and the first requirement and second requirement of the present invention were not satisfied, the toluene decomposition rate after the additional heat treatment was 90% or less. The deterioration rate after the additional heat treatment was greater than 6.5% in the honeycomb-structured catalysts of Sample No. 11. In the honeycomb-structured catalyst of Sample No. 8, the deterioration rate after the additional heat treatment was 1.8% to be low but the toluene decomposition rates before and after the additional heat treatment were 90% or less, more specifically 85.9% or less to be a low value.

The honeycomb-structured catalysts of Sample Nos. 12 to 15 are samples in which the composition x is 1.050 and the compositions y and z are different from one another. In the honeycomb-structured catalysts of Sample Nos. 13 and 14 which satisfied the first requirement and second requirement of the present invention, the toluene decomposition rates before and after the additional heat treatment were greater than 90% and the deterioration rate after the additional heat treatment was a value lower than 6.5%, specifically 1.6% or less.

In contrast, in the honeycomb-structured catalysts of Sample Nos. 12 and 15 in which the composition z was out of the range of $0.05 \leq z \leq 0.2$ and the first requirement and second requirement of the present invention were not satisfied, the toluene decomposition rate after the additional heat treatment was 90% or less. The deterioration rate after the additional heat treatment was greater than 6.5% in the honeycomb-structured catalysts of Sample No. 15. In the honeycomb-structured catalyst of Sample No. 12, the deterioration rate after the additional heat treatment was 1.0% to be low but the toluene decomposition rates before and after the additional heat treatment were 90% or less, more specifically 87.8% or less to be a low value.

The honeycomb-structured catalysts of Sample Nos. 9 and 13 are samples in which the first requirement and second requirement of the present invention are satisfied, the compositions y and z are the same as each other, but the composition x is different from each other. The honeycomb-structured catalysts of Sample Nos. 10 and 14 are samples in which the first requirement and second requirement of the present invention are satisfied, the compositions y and z are the same as each other, but the composition x is different from each other. Among these honeycomb-structured catalysts for organic substance decomposition, in the honeycomb-structured catalysts of Sample Nos. 13 and 14 in which x satisfied the relation of $x \geq 1.005$, the deterioration rate after the additional heat treatment was lower than that in the honeycomb-structured catalysts of Sample Nos. 9 and 10 in which x did not satisfy the relation of $x \geq 1.005$. Hence, in the honeycomb-structured catalyst for decomposing an organic substance which satisfies at least either of the first requirement or second requirement of the present invention, it is preferable that the composition x further satisfies the relation of $x \geq 1.005$.

The honeycomb-structured catalysts of Sample Nos. 5 and 16 to 22 are samples in which the composition is the same as one another but the firing temperature is different from one another. In the honeycomb-structured catalysts of Sample Nos. 5 and 17 to 21 which satisfied the first requirement and second requirement of the present invention, the toluene decomposition rates before and after the additional heat treatment were greater than 90% and the deterioration rate after the additional heat treatment was a value lower than 6.5%, specifically 2.0% or less.

In contrast, in the honeycomb-structured catalyst of Sample No. 16 fired at a firing temperature of 1000° C., the combustion at the time of production was insufficient and the honeycomb structure was not able to be maintained.

In the honeycomb-structured catalyst of Sample No. 22 fired at a firing temperature of 1700° C., a great number of defects such as cracks were generated by contraction at the time of firing and a favorable honeycomb structure was not able to be obtained.

The honeycomb-structured catalysts of Sample Nos. 16 and 22 were not able to be subjected to the measurement and evaluation of the toluene decomposition rate and deterioration rate since the catalysts were not able to maintain the honeycomb structure or had a structure with a great number of defects such as cracks. In other words, the honeycomb-structured catalysts of Sample Nos. 16 and 22 are samples which did not satisfy the first requirement and second requirement of the present invention. From the results described above, it is preferable that the firing temperature when producing the honeycomb-structured catalyst for decomposing an organic substance is 1050° C. or more and 1650° C. or less.

Subsequently, the honeycomb-structured catalysts of Sample Nos. 23 to 42 presented in Table 2 were fabricated for the purpose of confirming the properties when the composition of catalyst was changed. Here, in addition to the raw material powders used when fabricating the supported catalyst of Sample Nos. 1 to 21 in Table 1, high-purity $SrCO_3$ powder, $Co_3O_4$ powder, NiO powder, and $Fe_2O_3$ powder were prepared, and perovskite-type composite oxides were fabricated so as to have the compositions presented in Table 2. The method for evaluating the honeycomb-structured catalysts for organic substance decomposition fabricated is the same as the evaluation method described above.

TABLE 2

| Sample No. | Charged composition ratio | | | | A (x) | | B (y) | M (z) | | | |
|---|---|---|---|---|---|---|---|---|---|---|---|
| | x | y | z | y + z | Ba | Sr | Zr | Mn | Co | Ni |
| 23* | 1.000 | 0.900 | 0.100 | 1.000 | 1.000 | | 1.000 | | 1.000 | |
| 24 | 1.001 | 0.900 | 0.100 | 1.000 | 1.000 | | 1.000 | | 1.000 | |
| 25 | 1.005 | 0.900 | 0.100 | 1.000 | 1.000 | | 1.000 | | 1.000 | |
| 26 | 1.005 | 0.800 | 0.200 | 1.000 | 1.000 | | 1.000 | | 1.000 | |
| 27* | 1.005 | 0.600 | 0.400 | 1.000 | 1.000 | | 1.000 | | 1.000 | |
| 28* | 1.000 | 0.900 | 0.100 | 1.000 | 1.000 | | 1.000 | 0.400 | 0.400 | 0.100 |
| 29 | 1.001 | 0.900 | 0.100 | 1.000 | 1.000 | | 1.000 | 0.400 | 0.400 | 0.100 |
| 30 | 1.005 | 0.900 | 0.100 | 1.000 | 1.000 | | 1.000 | 0.400 | 0.400 | 0.100 |
| 31 | 1.005 | 0.800 | 0.200 | 1.000 | 1.000 | | 1.000 | 0.400 | 0.400 | 0.100 |
| 32* | 1.005 | 0.600 | 0.400 | 1.000 | 1.000 | | 1.000 | 0.400 | 0.400 | 0.100 |
| 33* | 1.000 | 0.900 | 0.100 | 1.000 | | 1.000 | 1.000 | 1.000 | | |
| 34 | 1.001 | 0.900 | 0.100 | 1.000 | | 1.000 | 1.000 | 1.000 | | |
| 35 | 1.005 | 0.900 | 0.100 | 1.000 | | 1.000 | 1.000 | 1.000 | | |
| 36 | 1.005 | 0.800 | 0.200 | 1.000 | | 1.000 | 1.000 | 1.000 | | |
| 37* | 1.005 | 0.600 | 0.400 | 1.000 | | 1.000 | 1.000 | 1.000 | | |
| 38* | 1.000 | 0.900 | 0.100 | 1.000 | 0.500 | 0.500 | 1.000 | 0.700 | 0.200 | 0.050 |
| 39 | 1.001 | 0.900 | 0.100 | 1.000 | 0.500 | 0.500 | 1.000 | 0.700 | 0.200 | 0.050 |
| 40 | 1.005 | 0.900 | 0.100 | 1.000 | 0.500 | 0.500 | 1.000 | 0.700 | 0.200 | 0.050 |
| 41* | 1.005 | 0.600 | 0.400 | 1.000 | 0.500 | 0.500 | 1.000 | 0.700 | 0.200 | 0.050 |

| Sample No. | M (z) Fe | Firing temperature (° C.) | Toluene decomposition rate (%) | | Deterioration rate (%) |
|---|---|---|---|---|---|
| | | | Before additional heat treatment | After additional heat treatment | |
| 23* | | 1500 | 96.0 | 84.2 | 12.3 |
| 24 | | 1500 | 96.9 | 92.2 | 4.9 |
| 25 | | 1500 | 97.4 | 95.1 | 2.4 |
| 26 | | 1500 | 98.9 | 95.4 | 3.5 |
| 27* | | 1500 | 93.3 | 79.2 | 15.1 |
| 28* | 0.100 | 1500 | 96.8 | 77.3 | 20.1 |
| 29 | 0.100 | 1500 | 97.2 | 93.1 | 4.2 |
| 30 | 0.100 | 1500 | 98.1 | 95.1 | 3.1 |
| 31 | 0.100 | 1500 | 98.5 | 95.2 | 3.4 |
| 32* | 0.100 | 1500 | 92.0 | 73.2 | 20.4 |
| 33* | | 1400 | 92.9 | 72.3 | 22.2 |
| 34 | | 1400 | 93.5 | 90.1 | 3.6 |
| 35 | | 1400 | 93.8 | 91.2 | 2.8 |
| 36 | | 1400 | 96.1 | 90.2 | 6.1 |
| 37* | | 1400 | 91.0 | 73.0 | 19.8 |
| 38* | 0.050 | 1450 | 94.6 | 80.6 | 14.8 |
| 39 | 0.050 | 1450 | 95.9 | 90.3 | 5.8 |
| 40 | 0.050 | 1450 | 96.9 | 90.8 | 6.3 |
| 41* | 0.050 | 1450 | 96.1 | 80.9 | 15.8 |

In Table 2, samples in which * is attached to Sample No. are samples which do not satisfy both of the first requirement and second requirement of the present invention described above and samples in which * is not attached to Sample No. are samples which satisfy both of the first requirement and the second requirement of the present invention described above.

The honeycomb-structured catalysts of Sample Nos. 23 to 27 are samples in which A of the perovskite-type composite oxide represented by $A_xB_yM_zO_w$ is Ba, B is Zr, and M is Co. In the honeycomb-structured catalysts of Sample Nos. 24 to 26 which satisfied the first requirement and second requirement of the present invention, the toluene decomposition rates before and after the additional heat treatment were greater than 90% and the deterioration rate after the additional heat treatment was a value lower than 6.5%.

Among the honeycomb-structured catalysts of Sample Nos. 24 to 26 which satisfied the first requirement and second requirement of the present invention, in the honeycomb-structured catalysts of Sample Nos. 25 and 26 in which the composition x satisfied the relation of $x \geq 1.005$, the deterioration rate after the additional heat treatment was 3.5% or less to be still lower, the toluene decomposition rate before the additional heat treatment was 97.4% or more, and the toluene decomposition rate after the additional heat treatment was 95.1% or more to be great. Hence, in the honeycomb-structured catalyst for decomposing an organic substance which satisfies at least either of the first requirement or second requirement of the present invention, it is preferable that the composition x further satisfies the relation of $x \geq 1.005$.

In contrast, in the honeycomb-structured catalysts of Sample Nos. 23 and 27 in which the composition x was out of the range of $1.001 \leq x \leq 1.05$ or the composition z was out of the range of $0.05 \leq z \leq 0.2$ and the first requirement and second requirement of the present invention were not satisfied, the toluene decomposition rate after the additional heat treatment was 90% or less and the deterioration rate after the additional heat treatment was greater than 6.5%.

The honeycomb-structured catalysts of Sample Nos. 28 to 32 are samples in which A of the perovskite-type composite oxide represented by $A_xB_yM_zO_w$ is Ba, B is Zr, and M is Mn, Co, Ni, and Fe. In the honeycomb-structured catalysts of Sample Nos. 29 to 31 which satisfied the first requirement and second requirement of the present invention, the toluene decomposition rates before and after the additional heat treatment were greater than 90% and the deterioration rate after the additional heat treatment was a value lower than 6.5%.

Among the honeycomb-structured catalysts of Sample Nos. 29 to 31 which satisfied the first requirement and second requirement of the present invention, in the honeycomb-structured catalysts of Sample Nos. 30 and 31 in which the composition x satisfied the relation of $x \geq 1.005$, the deterioration rate after the additional heat treatment was 3.4% or less to be still lower, the toluene decomposition rate before the additional heat treatment was 98.1% or more, and the toluene decomposition rate after the additional heat treatment was 95.1% or more to be great. Hence, in the honeycomb-structured catalyst for decomposing an organic substance which satisfies the first requirement and second requirement of the present invention, it is preferable that the composition x further satisfies the relation of $x \geq 1.005$.

In contrast, in the honeycomb-structured catalysts of Sample Nos. 28 and 32 in which the composition x was out of the range of $1.001 \leq x \leq 1.05$ or the composition z was out of the range of $0.05 \leq z \leq 0.2$ and the first requirement and second requirement of the present invention were not satisfied, the toluene decomposition rate after the additional heat treatment was 90% or less and the deterioration rate after the additional heat treatment was greater than 6.5%.

The honeycomb-structured catalysts of Sample Nos. 33 to 37 are samples in which A of the perovskite-type composite oxide represented by $A_xB_yM_zO_w$ is Sr, B is Zr, and M is Mn. In the honeycomb-structured catalysts of Sample Nos. 34 to 36 which satisfied the first requirement and second requirement of the present invention, the toluene decomposition rates before and after the additional heat treatment were greater than 90% and the deterioration rate after the additional heat treatment was a value lower than 6.5%.

Among the honeycomb-structured catalysts of Sample Nos. 34 to 36 which satisfied the first requirement and second requirement of the present invention, in the honeycomb-structured catalysts of Sample Nos. 35 and 36 in which the composition x satisfied the relation of $x \geq 1.005$, the toluene decomposition rate before the additional heat treatment was 93.8% or more and the toluene decomposition rate after the additional heat treatment was 90.2% or more to be still greater.

Hence, in the honeycomb-structured catalyst for decomposing an organic substance which satisfies the first requirement and second requirement of the present invention, it is preferable that the composition x further satisfies the relation of $x \geq 1.005$.

In contrast, in the honeycomb-structured catalysts of Sample Nos. 33 and 37 in which the composition x was out of the range of $1.001 \leq x \leq 1.05$ or the composition z was out of the range of $0.05 \leq z \leq 0.2$ and the first requirement and second requirement of the present invention were not satisfied, the toluene decomposition rate after the additional heat treatment was 90% or less and the deterioration rate after the additional heat treatment was greater than 6.5%.

The honeycomb-structured catalysts of Sample Nos. 38 to 41 are samples in which A of the perovskite-type composite oxide represented by $A_xB_yM_zO_w$ is Ba and Sr, B is Zr, and M is Mn, Co, Ni, and Fe. In the honeycomb-structured catalysts of Sample Nos. 39 and 40 which satisfied the first requirement and second requirement of the present invention, the toluene decomposition rates before and after the additional heat treatment were greater than 90% and the deterioration rate after the additional heat treatment was a value lower than 6.5%.

Between the honeycomb-structured catalysts of Sample Nos. 39 and 40 which satisfied the first requirement and second requirement of the present invention, in the honeycomb-structured catalyst of Sample No. 40 in which the composition x satisfied the relation of $x \geq 1.005$, the toluene decomposition rate before the additional heat treatment was 96.9% and the toluene decomposition rate after the additional heat treatment was 90.8% to be still greater. Hence, in the honeycomb-structured catalyst for decomposing an organic substance which satisfies the first requirement and second requirement of the present invention, it is preferable that the composition x further satisfies the relation of $x \geq 1.005$.

In contrast, in the honeycomb-structured catalysts of Sample Nos. 38 and 41 in which the composition x was out of the range of $1.001 \leq x \leq 1.05$ or the composition z was out of the range of $0.05 \leq z \leq 0.2$ and the first requirement and second requirement of the present invention were not satisfied, the toluene decomposition rate after the additional heat treatment was 90% or less and the deterioration rate after the additional heat treatment was greater than 6.5%.

In Tables 1 and 2, samples in which * is not attached to Sample No. satisfy both of the first requirement and the second requirement of the present invention described above, but an effect is exerted that the organic substance decomposition rate is high and the deterioration due to a heat treatment at a high temperature can be suppressed as long as at least either of the first requirement or the second requirement is satisfied.

Comparative Example

A comparison was conducted between the honeycomb-structured catalysts for organic substance decomposition of the present invention and a honeycomb-structured catalyst in which the catalyst was supported on a carrier having a honeycomb structure. Specifically, a perovskite-type composite oxide was fabricated by the same method as the method for fabricating the sample of Sample No. 5 in Table 1, 320 g of pure water was added to 450 g of the perovskite-type composite oxide fabricated, and appropriate amounts of an organic dispersant and an antifoaming agent were further added thereto, and the mixture was wet-mixed together with $ZrO_2$ cobble stones for 2 hours to obtain a catalyst slurry.

A ceramic honeycomb serving as a carrier was immersed in the obtained catalyst slurry for 1 minute. The ceramic honeycomb is formed of porous cordierite. The external shape of the ceramic honeycomb is the same as the external shape of the honeycomb-structured catalyst for decomposing an organic substance illustrated in FIG. 1, and the size thereof is as follows: the dimension in the X-axis direction in FIG. 1 is about 40 mm, the dimension in the Y-axis direction is about 40 mm, and the dimension in the Z-axis direction is about 50 mm. The size of the cell in the Z-axis direction in plan view is about 1.5 mm×about 1.5 mm, and the number of cells per 1 $inch^2$ is about 200.

A great number of pores are provided at the portion other than the cells of the ceramic honeycomb. The pore diameter is, for example, 0.3 μm or more and 50 μm or less, the average diameter is 3 μm, and the volume porosity is about 50%. The diameter of pores is an equivalent circle diameter.

After the immersion of the ceramic honeycomb in the catalyst slurry, the excess catalyst slurry remaining in the ceramic honeycomb was blown off with an air stream, and then the ceramic honeycomb was dried at 120° C. for 12 hours in a dryer. Thereafter, the ceramic honeycomb was fired in the air at 1000° C. for 3 hours in an electric furnace to obtain a honeycomb-structured catalyst for comparison. In this honeycomb-structured catalyst for comparison, catalyst particles are supported on the inner wall of the cells of the ceramic honeycomb which is a carrier.

The properties of the honeycomb-structured catalyst for comparison obtained after being subjected to a heat treatment at a high temperature were examined by the same method as the evaluation method described above. In other words, when the honeycomb-structured catalyst for comparison was subjected to a heat treatment at 1200° C. for 48 hours in an electric furnace and then the toluene decomposition rate was determined, the result was a low value of 60%. This is considered to be caused by the chemical reaction between cordierite of the ceramic honeycomb and the catalyst during the heat treatment.

In other words, the honeycomb-structured catalyst for comparison in which a catalyst containing a perovskite-type composite oxide having the same composition as the honeycomb-structured catalyst for decomposing an organic substance of the present invention was supported on a carrier having a honeycomb structure was greatly deteriorated when being subjected to a heat treatment at a high temperature of 1200° C. and the organic substance decomposition rate significantly decreased.

In contrast, in the honeycomb-structured catalyst for decomposing an organic substance of the present invention, a carrier and a binder for supporting the catalyst on the carrier are not used, thus a chemical reaction between the carrier material or the binder and the catalyst material does not occur, and the deterioration due to a heat treatment at a high temperature can be suppressed. Hence, the honeycomb-structured catalyst for decomposing an organic substance of the present invention can be used in a high temperature environment. For example, even when cooling equipment is required in the case of using a conventional catalyst, such cooling equipment can be omitted in the case of using the honeycomb-structured catalyst for decomposing an organic substance of the present invention, and this can contribute to simplification of the equipment.

The present invention is not limited to the embodiments, and various applications and modifications can be added within the scope of the present invention.

In the above description, an example in which toluene is decomposed using the honeycomb-structured catalyst for decomposing an organic substance of the present invention has been described, but the organic substance is not limited to toluene.

In the above description, a honeycomb-structured catalyst for decomposing an organic substance is fabricated by extrusion molding using a kneaded product containing catalyst particles but may be fabricated by other fabricating methods. For example, a honeycomb-structured catalyst for decomposing an organic substance may be fabricated by a 3D printer (three-dimensional modeling apparatus) using a material containing catalyst particles.

DESCRIPTION OF REFERENCE SYMBOLS

- 10: Ceramic honeycomb
- 20: Catalyst sample for test
- 30: Testing apparatus
- 31: Pipe
- 32: Heating unit
- 33: Control unit
- 34: Gas supply pipe
- 35: Gas discharge pipe
- 36: Toluene supply line
- 37: Nitrogen supply line
- 38: Oxygen supply line
- 39: Sampling line
- 41: Reaction pipe
- 42: Heat-resistant inorganic adhesive

The invention claimed is:

1. A honeycomb-structured catalyst for decomposing an organic substance, the honeycomb-structured catalyst comprising:
   a catalyst particle that contains a perovskite-type composite oxide represented by $A_xB_yM_zO_w$, where the A contains at least one selected from Ba and Sr, the B contains Zr, the M is at least one selected from Mn, Co, Ni, and Fe, y+z=1, 1.001≤x≤1.05, 0.05≤z≤0.2, and w is a positive value that satisfies electrical neutrality, and
   a toluene decomposition rate is greater than 90% when toluene is decomposed using the honeycomb-structured catalyst subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C.

2. The honeycomb-structured catalyst for decomposing an organic substance according to claim 1, wherein 1.001≤x≥1.005.

3. The honeycomb-structured catalyst for decomposing an organic substance according to claim 1, wherein the honeycomb-structured catalyst is an extrusion molded catalyst.

4. An organic substance decomposing apparatus comprising a flow path for an organic substance, and the honeycomb-structured catalyst for decomposing an organic substance according to claim 1.

5. The organic substance decomposing apparatus according to claim 4, wherein $1.001 \leq x \geq 1.005$.

6. The organic substance decomposing apparatus according to claim 4, wherein the honeycomb-structured catalyst is an extrusion molded catalyst.

7. A honeycomb-structured catalyst for decomposing an organic substance, the honeycomb-structured catalyst comprising:
a catalyst particle that contains a perovskite-type composite oxide represented by $A_xB_yM_zO_w$, where the A contains at least one selected from Ba and Sr, the B contains Zr, the M is at least one selected from Mn, Co, Ni, and Fe, $y+z=1$, $1.001 \leq x \leq 1.05$, $0.05 \leq z \leq 0.2$, and w is a positive value that satisfies electrical neutrality, and
when a toluene decomposition rate is regarded as 1 when toluene is decomposed using the honeycomb-structured catalyst before being subjected to a heat treatment at 1200° C. for 48 hours and a gas that contains 50 ppm toluene, 80% nitrogen, and 20% oxygen as a volume concentration as a target at a space velocity of 30,000/h and a catalyst temperature of 400° C., the toluene decomposition rate when using the honeycomb-structured catalyst after being subjected to the heat treatment is greater than 0.935 and smaller than 1.

8. The honeycomb-structured catalyst for decomposing an organic substance according to claim 7, wherein the x satisfies a relation of $x \geq 1.005$.

9. The honeycomb-structured catalyst for decomposing an organic substance according to claim 7, wherein the honeycomb-structured catalyst is an extrusion molded catalyst.

10. An organic substance decomposing apparatus comprising a flow path for an organic substance, and the honeycomb-structured catalyst for decomposing an organic substance according to claim 7.

11. The organic substance decomposing apparatus according to claim 10, wherein $1.001 \leq x \geq 1.005$.

12. The organic substance decomposing apparatus according to claim 10, wherein the honeycomb-structured catalyst is an extrusion molded catalyst.

* * * * *